United States Patent [19]
Breivik et al.

[11] Patent Number: 6,090,546
[45] Date of Patent: Jul. 18, 2000

[54] METHOD FOR THE DETECTION OF RAS ONCOGENES, IN PARTICULAR THE K-RAS ONCOGENE

[75] Inventors: Jarle Breivik; Gustav Gaudernack, both of Oslo, Norway

[73] Assignee: Medinnova SF, Oslo, Norway

[21] Appl. No.: 08/836,329

[22] PCT Filed: Nov. 10, 1995

[86] PCT No.: PCT/GB95/02644

§ 371 Date: Aug. 22, 1997

§ 102(e) Date: Aug. 22, 1997

[87] PCT Pub. No.: WO96/15262

PCT Pub. Date: May 23, 1996

[30] Foreign Application Priority Data

Nov. 11, 1994 [GB] United Kingdom .................. 9422814

[51] Int. Cl.⁷ ...................................... C12Q 1/68
[52] U.S. Cl. ................... 435/6; 536/24.31; 536/24.32
[58] Field of Search .............. 435/5; 536/24.31, 536/24.32

[56] References Cited

U.S. PATENT DOCUMENTS 4,654,267  3/1987  Ugelstad et al. ................. 423/407

FOREIGN PATENT DOCUMENTS

| 0466083 | 1/1992 | European Pat. Off. | ........ C12N 15/10 |
| 0537008 | 4/1993 | European Pat. Off. | ........ A61K 31/66 |
| 4-235919 | 8/1992 | Japan | ........ A61K 31/70 |
| 90/11369 | 10/1990 | WIPO | ........ C12Q 1/68 |
| 92/14756 | 9/1992 | WIPO | ........ C07K 13/00 |
| 92/15680 | 9/1992 | WIPO | ........ C12N 15/11 |
| 95/13368 | 5/1995 | WIPO | ........ C12N 15/10 |

OTHER PUBLICATIONS

The Stratagene Catalog, p. 39, 1988.
Andersen, S.N., et al., "K–ras mutations and HLA–DR expression in large bowel adenomas", *Br. J of Cancer*, 74, 99–108, (1996).
Andersen, S.N., et al., "K–ras mutations and Prognosis in Large–Bowel Carcinomas", *Scand. J. Gastroenterol.*, 32, 62–69, (1996).
Benhattar, J., et al., "Prognostic Significance of K–ras Mutations in Colorectal Carcinoma", *Gastroenterology*, 104, 1044–1048, (1993).
Chen, J., et al., "A Method to Detect ras Point Mutations in Small Subpopulations of Cells", *Analytical Biochemistry*, 195, 51–56, (1991).
Haliassos, A., et al., "Detection of minority point mutations by modified PCR technique: a new approach for a sensitive diagnosis of tumor–progression markers", *Nucleic Acids Research*, 17, 8093–8099, (1989).
Haliassos, A., et al., "Modification of enzymatically amplified DNA for the Detection of Point Mutations", *Nucleic Acids Research*, 17, 9, 3606, (1989).
Jackson, P.E., et al., "Frequency of Ki–ras mutations and DNA alkylation in colorectal tissue from individuals living in Manchester", *Molecular Carcinogenesis*, 16, 12–19, (1996).
Jacobson, D.R., et al., "A Highly Sensitive Assay for Mutant ras Genes and Its Application to the Study of Presentation and Relapse Genotype in acute Leukemia", *Oncogene*, 9, 553–563, (1994).
Jacobson, D.R., et al., "Rapid, nonradioactive screening for activating ras onocogene mutations using PCR–primer introduced restriction analysis (PCR–PIRA)", *PCR Methods and Applications*, Cold Spring Harbor Laboratory Press, 146–148, (1991).
Kahn, S.M., et al., "Rapid and sensitive nonradioactive detection of mutant K–ras genes via 'enriched' PCR amplification", *Oncogene*, 6, 1079–1083, (1991).
Kahn, S.M., et al., "Rapid Nonradioactive Detection of ras Oncogenes in Human Tumors", *Amplifications*, 4, 22–26, (May, 1990).
Kumar, R., et al., "Oncogene Detection at the single cell level", *Oncogene*, 3, 647–651, (1988).
Levi, S., et al., "Multiple K–ras codon 12 mutations in cholangiocarcinomas demonstrated with a sensitive polymerase chain reaction technique", *Can. Res.*, 51, 3497–3502, (1991).
Lin, S., et al., "Mutation analysis of K–ras Oncogenes in Gastroenterologic Cancers by the Amplified Created Restriction Sites Method", *Am. J of Clin. Pathology*, 100, 6, 686–689, (1993).
Mitsudomi, T., et al., "Mutations of ras genes distinguish a subset of non–small–cell lung cancer cell lines from small–cell lung cancer cell lines", *Oncogene*, 6, 8, 1353–1362, (1991).
Pretlow, T.P., et al., "K–ras mutations in putative preneoplastic lesions in human colon", *J of Natl. Cancer Inst.*, 85, 24, 2004–2007, (1993).
Rosell, R., et al., "Prognostic impact of mutated K–ras gene in surgically resected non–small cell lung cancer patients", *Oncogene*, 8, 2407–2412, (1993).
Suchy, B., et al., "K–ras Point Mutations in Human Colorectal Carcinomas: Related to Aneuploidy and Metastasis", *Int. J. Cancer*, 52, 30–33, (1992).
Urban, T., et al., "Detection of c–Ki–ras mutation by PCR/RFLP analysis and diagnosis of pancreatic adenocarcinomas", *J of the Natl. Cancer Inst.*, 85, 24, 2008–2012, (1993).

*Primary Examiner*—Scott W. Houtteman
*Attorney, Agent, or Firm*—Schwegman, Lundberg, Woessner & Kluth, P.A.

[57] ABSTRACT

The invention relates to an oligonucleotide primer sequence for use in in vitro amplification, characterised in that said primer sequence is capable of creating a BstX I restriction site overlapping codon (12) and/or an Xcm I restriction site overlapping codon (13) or a Bce 83I restriction site overlapping codon (61) of the wild-type K-ras oncogene, methods of using said primer sequences for detecting activating mutations in codons (12 and/or 13 and/or 61) of the K-ras oncogene and kits for performing the methods.

20 Claims, 28 Drawing Sheets

CCGGGGTCCGGTCCCGCTCCGGTCAGAATTGGCGTGCGGGACAGCCTTGCGGCTAGGCAGGGGGCCCGCCGTGGG
TCCGGCAGTCCCTCCTCCTCCCGCCAAGGCGCCGCCCAGACCCGCTCTCCAGCCGCTCGCCACCCTAGACCCCAGCC
ACCCCTTCCTCCGCGGCCCCGCTCTCCCCCGCCCCCTCCTTCTCCGCGGCTCCGCTGC
CTCCCCCTCTTCCCTCTTCCCTCCCTCTCAGCCGCCCTCCCCTCTCGTACGCCCTCTGAAGAAGAATCGAGCGCGAACGCA
TGGATAGCTCTGCCCTCTGGGCCCCGGCCGAACTCATCGTGTGCTCGGAGCTCGATTTTCCTAGGCGGCGGCGGC
GGCGGAGGCAGCAGCGGGCCGAAGGTGGCGGCAGTGCCTCGGCCAGTACTCCCGGCCCCCGCCATTTCGG
ACTGGAGGCGAGCGGCCAGGCACTGAAGGCTCAGAGGCTCCCAGTGCGGGAGAGAGGTACGG
                                                                    ←EXON 0
AGCGGACCACCCCTCCTGCCCGGTCCCGACCCTCTTTGCCCGGCCGGGGCCGGCCGGCGAGTGAATGAAT
TAGGGGTCCCGGAGGGCGGGTCGGCGCGGGGTCGGGTGAGAGGGGTCTGCAG>>>GTACTGGT
GGAGTATTTGATAGTGTATTAACCTTATGTGTGACATGTTCTAATATAGTCACATTTTCATTATTTTATTATAAG GCCTGC
                                                                            EXON 1→

Met Thr Glu Tyr Lys Leu Val Val Val Gly Ala Gly Gly Val Gly Lys Ser Ala Leu Thr
TGAAA ATG ACT GAA TAT AAA CTT GTG GTA GTT GGA GCT GGT GGC GTA GGC AAG AGT GCC TTG ACG
                                           12  13

Ile Gln Leu Ile Gln Asn His Phe Val Asp Glu Tyr Asp Pro Thr Ile Glu
ATA CAG CTA ATT CAG AAT CAT TTT GTG GAC GAA TAT GAT CCA ACA ATA GAG GTAAATCTTGTTT
                                                                  ←EXON 1

FIG. 1A

```
TAATATGCATATTACTGGTGCAGGACCATTCTTTGATACAGATAAAGGTTTCTCTGACCATTTTCATGAGT>>>ATCACCATTT
TACATTCCCACCAGCAATGCACAAAGATTTCAGTGCTCCTTGCTGTATCCTTGCTGTATCCTGCTCTATTTCCATTTTTGAGTTTTTTTGTT
TTGTTTTTTAATAATAGCCAATCCTAAGTGGTATGTGGTAGCATCTCATGGTTTGATTTTATTTCCTGACTATTGATGATG
TTGAGCATCTTTTCAGGTGCTAGTGGCCATTGTCCGTCATCTTGGAGCAGGAACAATGTCTTTCAAGTCCTTTGCCAT
TTTTAAATTGAATTTTTTGTTGTTGAGTGTATATAACACCTTTTTGAAGTAAAGGTGCACTGTAATAATCCAGACTGTGTT
                 Asp Ser Tyr Arg Lys Gln Val Val Ile Asp Gly Glu Thr Cys Leu Leu Asp
TCTCCCTTCTCAG GAT TCC TAC AGG AAG CAA GTA GTA ATT GAT GGA GAA ACC TGT CTC TTG GAT
    EXON 2 →
                                        61
Ile Leu Asp Thr Ala Gly Gln Glu Glu Tyr Ser Ala Met Arg Asp Gln Tyr Met Arg Thr Gly
ATT CTC GAC ACA GCA GGT CAA GAG GAG TAC AGT GCA ATG AGG GAC CAG TAC ATG AGG ACT GGG
Glu Gly Phe Leu Cys Val Phe Ala Ile Asn Asn Thr Lys Ser Phe Glu Asp Ile His His Tyr
GAG GGC TTT CTT TGT GTA TTT GCC ATA AAT AAT ACT AAA TCA TTT GAA GAT ATT CAC CAT TAT
Ar                                                                            ←EX
AG GTGGGTTTAAATTGAATATAATAAGCTGACATTAAGGAGTAATTATAGTTTTTATTTTTTGAGTCTTTGCTAATGCCATGC
  ON 2
ATATAATATTTAATAAAAATTTTAAATAATGTTTATGAGGTAGTAATATCCCGTTTATAAATGAAGTTCTTGGGGATT
AGAGCAGTGGAGTAACTTGCTCCAGACTGCATCGGTAGTGGTGCTGGGATTGAAACCTAGGCCTGTTGACTCCACAGCCT
TCTGT>>>TCTAGAATTTTTCAGTAGTTTCGTTTTGTCTGCATATTAACCTATTAGGTTATAGTTTTAC
TATACTTCTAGGTATTTGATCTTTGAGAGAGATACAAGGTTTCTGTTTAAAAAGGTAAGAAACAAAATAACTAGAAGAA
GGAAGGAAAATTTGGTGTAGTGGAAACTAGGAATTACATTGTTTCTTTTCAGCCAAATTTTATGACAAAGTTGTGGACAGGT
```

FIG. 1B

```
                                                      g Glu Gln Ile Lys Arg Val
TTTGAAAGATATTTGTGTTACTAATGACTGTGCTATAACTTTTTTCTTTCCCAG A GAA CAA ATT AAA AGA GTT
                                                       EXON 1→

Lys Asp Ser Glu Asp Val Pro Met Val Leu Val Gly Asn Lys Cys Asp Leu Pro Ser Arg Thr
AAG GAT TCT GAA GAT GTA CCT ATG GTC CTA GTA GGA AAT AAA TGT GAT TTG CCT TCT AGA ACA

Val Asp Thr Lys Gln Ala Gln Asp Leu Ala Arg Ser Tyr Gly Ile Pro Phe Ile Gly Thr Ser
GTA GAC ACA AAA CAG GCT CAG GAC TTA GCA AGA AGT TAT GGA ATT CCT TTT ATT GGA ACA TCA

Ala Lys Thr Arg Gln
GCA AAG ACA AGA CAG GTAAGTAACACTGAAATAAATACAGATCTGTTTCTGCAAATCATAACTGTTATGTCATTTA
              ←EXON 1
ATATATCAGTTTTTCTCTCAATTATGCTATACTAGGAAATAAAACAATATTTGTCTCTTGAGAGGGCATTG
CTTCTTAATC>>ACAGAGACCCAGTCTCACTTGTATACCCTGAAATAGACTGAAAGGTGTTAAATTTAAAATAA
AACTCAAGGTTCCAGTTCTTGACTCACCTTTGAGATTCTTTTGTTTTTGTGTTTTAACAAAGGTTTCACGTCCATATT
TTACCCATTTTCTTCCTCATTCTCCCCTGGAGGAGGGTGTGGGAATCGATAGTATATAAATCACTTTTTTCCTAAGTCAAAGAA
GTAATTTAAAGCTAACTTCAGTTTAGGCTTTCATAATCTCCTAATTCCTAATTTAAAAATTTAAAATTTAATTGACAAACAGATGCTA
ATACCTGTGTTAGGCTAACTTCAGTTTGTCATAATCTCCTAGCCCATATTTAAACTGCATCCTCAGTTTATTCAAACAGTCTGATGTCTGTTTAA
GACTTTTAAGAACAAACCAGGATTCTAGCCCATATTTAAACTGCATCCTCAGTTTATTCAAACAGTCTGATGTCTGTTTAA
AAAAAAAATCTCAAGCTCATAATCTCAAACTTCTTGCACATGGCTTTCCCAGTAAATTACTCTTACCAATGCAACAGACT
```

FIG. 1C

```
                                                                Arg Val Glu Asp Ala Phe Tyr Thr Leu Val Arg Glu Ile Arg
TTAAAGAAGTTGTGTTTACAATGCAG AGA GTG GAG GAT GCT TTT TAT ACA TTG GTG AGA GAG ATC CGA
                          EXON 4A→

Gln Tyr Arg Leu Lys Lys Ile Ser Lys Glu Glu Lys Thr Pro Gly Cys Val Lys Ile Lys Lys
CAA TAC AGA TTG AAA AAA ATC AGC AAA GAA GAA AAG ACT CCT GGC TGT GTG AAA ATT AAA AAA

Cys Ile Ile Met OC
TGC ATT ATA ATG TAA TCTG GTAAGTTTAAGTTCAGCACATTAATTTGGCAGAAAGCAGATGTCTTTAAAGTAACA
                       ←EXON 4A

AGGTGGCAACCACTTAGAACTACTAGGTGTAGTATTCTAACTTGAAGTATTAAAGATAAGAAACTTGTTTCCATAATTAG

T>>>GAATTCTAAAGTCCTAATATATGTAATATATTCAGTGCCTGAAGAGAAACATAAAGAATCCTTTCTTAATATTTT
                                                                               Gly
TCCATTAATGAAATTGTTACCTGTACACATGAAGCCATGCGTATATATTCACATTTAATACTTTTATGTATTCAG GGT
                                                                            EXON 4B

Val Asp Asp Ala Phe Tyr Thr Leu Val Arg Glu Ile Arg Lys His Lys Glu Lys Met Ser Lys
GTT GAT GAT GCC TTC TAT ACA TTA GTT CGA GAA ATT CGA AAA CAT AAA GAA AAG ATG AGC AAA

Asp Gly Lys Lys Lys Lys Lys Lys Ser Lys Thr Lys Cys Val Ile Met OC
GAT GGT AAA AAG AAG AAA AAG AAG TCA AAG ACA AAG TGT GTA ATT ATG TAA ATACAATTGTACTT
```

FIG. 1D

TTTTCTTAAGGCATACTAGTACAAG TGGTAATTTTTGTACATTACACTAAATTATTAGCATTTGTTTTAGCATTACCTAATTT
← EXON 4B

TTTCCTGCTCCATGCAGACTGTTAGCTTTTACCTTAAATGCTTATTTAAAATGACAGTGGAAGTTTTTTTCCTGAAGT

GCCAGTATTCCCAGAGTTTGGTTTTGAACTAGCAATGCCTGTGAAAAGAAACTGAATACCTAAGATTCTGTCTTGGGTT

TTTGGTGCATGCAGTTGATTACTTCTTATTTTCTTACCAAGTGTGAATGTTGGTGTGAAACAAATTAATGAAGCTT

FIG. 1E

```
                Xcm I
               CCA-----TGG
                        BstX I
                       CCA-----TGG

5K1
    [-------------------CCA----->

TGAAATGACTGAATATAAACTTGTGTAGTTGGAGCTGGTGGCGTAGGCAAGAGTGCCTTGACGATACAGCTAATTCAGAATCATTTTG>>>
ACTTTACTGACTTATATTTGAACACCATCAACCTCGACCACCGCATCCGTTCTCACGGAACTGCTATGTCGATTAAGTCTTAGTAAAAC<<<

>>>TGGACGAATATGATCCAACAATAGAGGTAAATCTTGTTTTAATATGCATATTACTGGTGCAGGACCATTCTTTGATACAGATAAAGGTTT
<<<ACCTGCTTATACTAGGTTGTTATCTCCATTTAGAACAAAATTATACGTATAATGACCACGTCCTGGTAAGAACTATGTCTATTTCCAAA

3K1
                                                   <----------]
                                              3K2
                                         <-----G-----C----]
                                                    Xcm I
                                                   CCA-----TGG
                                                      BstX I
                                                     CCA-----TGG

Primers:

5K1: ACTGAATATAAACTTGTGGTCCATGGAGCT

5K1-Bio: Biotin-ACTGAATATAAACTTGTGGTCCATGGAGCT

3K1: TTATCTGTATCAAAGAATGGTCCTGCACCA

3K2: GAATGGTCCTCCACCAGTAATATGGATATTA

3K3: TATTAAACAAGATTTAC

Endonucleases:

BstX I:  C C A N N N N N|N T G G
         G G T N|N N N N N A C C

Xcm I:  C C A N N N N N|N N N T G G
        G G T N N N|N N N N N A C C

FIG. 2B

PCR A₁

12 13
>>>>>>>>>>>>>>>>>>>>>>GGTGGC>>>>>>>>>>>>>>>>>>>>>>>>>>>>>>>>>>>>>>>>>>>>
ACTGAATATAAACTTGTGGT^CC A^TGGAGCT                    ACCACGTCCTGGTAAGAAACTATGTCTATT
<<<<<<<<<<<<<<<<<<<<<<<<<<CCACCG<<<<<<<<<<<<<<<<<<<<<<<<<<<<<<<<<<<<<<<<<

>>>>>>>>>>>>>>>>>>>>>>GATGGC>>>>>>>>>>>point mutation>>>>>>>>>>>>>>>>>>>
ACTGAATATAAACTTGTGGT^CC A^TGGAGCT                    ACCACGTCCTGGTAAGAAACTATGTCTATT
<<<<<<<<<<<<<<<<<<<<<<<<<<CTACCG<<<<<<<<<<<<<<<<<<<<<<<<<<<<<<<<<<<<<<<<

```
                                                                    PCR A2
10a   ACTGAATATAAACTTGTGGTCCATGGAGCTGGTGGC>>>>>>>>>>>>>>TGGTGCAGGACCATTCTTTGATACAGATAA
      TGACTTATATTTGAACACCAGGTACCTCGACCACCG                          ACCACGTCCTGGTAAGAAACTATGTCTATT

ACTGAATATAAACTTGTGGTCCATGGAGCTGATGGC>>>>>>>>>>>>>>ACCACGTCCTGGTAAGAAACTATGTCTATT
      TGACTTATATTTGAACACCAGGTACCTCGACTACCG<<<<<<<<<<<<<<<TGGTGCAGGACCATTCTTTGATACAGATAA
                                                          →

11a   ACTGAATATAAACTTGTGGTCCATGGAGCTGGTGGC>>>>>>>>>>>>>>TGGTGCAGGACCATTCTTTGATACAGATAA
      TGACTTATATTTGAACACCAGGTACCTCGACCACCG<<<<<<<<<<<<<<ACCACGTCCTGGTAAGAAACTATGTCTATT

ACTGAATATAAACTTGTGGTCCATGGAGCTGATGGC>>>>>>>>>>>>>>TGGTGCAGGACCATTCTTTGATACAGATAA
      TGACTTATATTTGAACACCAGGTACCTCGACTACCG<<<<<<<<<<<<<<ACCACGTCCTGGTAAGAAACTATGTCTATT
                                                          →
```

PCR A₂

10b:
```
ACTGAATATAAACTTGTGGTCCATGGAGCTGGTGGC>>>>>>>>>>>TGGTGCAGGACCATTCTTTGATACAGATAA
                                                ACCACGTCCTGGTAAGAAACTATGTCTATT

ACTGAATATAAACTTGTGGTCCATGGAGCT
TGACTTATATTTGAACACCAGGTACCTCGACCACCG<<<<<<<<<<<ACCACGTCCTGGTAAGAAACTATGTCTATT

ACTGAATATAAACTTGTGGTCCATGGAGCTGATGGC>>>>>>>>>>>TGGTGCAGGACCATTCTTTGATACAGATAA
                                                ACCACGTCCTGGTAAGAAACTATGTCTATT

ACTGAATATAAACTTGTGGTCCATGGAGCT
TGACTTATATTTGAACACCAGGTACCTCGACTACCG<<<<<<<<<<<ACCACGTCCTGGTAAGAAACTATGTCTATT
```

→

11b:
```
ACTGAATATAAACTTGTGGTCCATGGAGCTGGTGGC>>>>>>>>>>>TGGTGCAGGACCATTCTTTGATACAGATAA
TGACTTATATTTGAACACCAGGTACCTCGACCACCG<<<<<<<<<<<ACCACGTCCTGGTAAGAAACTATGTCTATT

ACTGAATATAAACTTGTGGTCCATGGAGCTGATGGC>>>>>>>>>>>TGGTGCAGGACCATTCTTTGATACAGATAA
TGACTTATATTTGAACACCAGGTACCTCGACTACCG<<<<<<<<<<<ACCACGTCCTGGTAAGAAACTATGTCTATT
```

Xcm I

```
                                                                                            16b
●ACTGAATATAAACTTGTGGTCCATGGAG CTGGTGGC>>>>>>>>>TAATATCCATATTA CTGGTCCACCACCATTC
 TGACTTATATTTGAACACCAGGTACCT CGACTACCG<<<<<<<<<ATTATAGGTATAA TGACCAGGTGGTGGTAAG

●ACTGAATATAAACTTGTGGTCCATGGAG CTGATGGC>>>>>>>>>TAATATCCATATTA CTGGTCCACCACCATTC
 TGACTTATATTTGAACACCAGGTACCT CGACTACCG<<<<<<<<<ATTATAGGTATAA TGACCAGGTGGTGGTAAG
```

→

```
                                        107bp                                       17b
●ACTGAATATAAACTTGTGGTCCATGGAG CTGGTGGC>>>>>>>>>TAATATCCATATTA CTGGTCCACCACCATTC
 TGACTTATATTTGAACACCAGGTACCT CGACTACCG<<<<<<<<<ATTATAGGTATAA TGACCACCTCCTGGTAAG

●ACTGAATATAAACTTGTGGTCCATGGAG CTGATGGC>>>>>>>>>TAATATCCATATTA CTGGTCCACCACCATTC
 TGACTTATATTTGAACACCAGGTACCT CGACTACCG<<<<<<<<<ATTATAGGTATAA TGACCACCTCCTGGTAAG
```

Codon 13 -

METHOD FOR THE DETECTION OF RAS ONCOGENES, IN PARTICULAR THE K-RAS ONCOGENE

The present invention relates to the detection of mutations in Ras oncogenes, and in particular in the K-ras gene.

Ras oncogenes are implicated in the development of a range of cancers. In particular somatically induced, activating mutations at defined positions in ras genes are believed to be important causative events in the process of tumorigenesis. Ras gene mutations occur in approximately 30% of human tumours, including cancer of the lung, thyroid, colon, rectum, pancreas and breast, and certain melanomas and leukaemias, although their incidence does vary according to tumour type. In addition, certain experimental tumour systems have been shown to be associated with activated ras genes. More specifically, mutations of the K-ras gene have been reported to be as high as 90% in carcinomas of the pancreas, 50% in adenocarcinomas of the lung and 40% in adenocarcinomas of the colon.

Activation of the ras oncogenes appears to be most frequently associated with mutations at position 12, although activation at other positions e.g. positions 13 and 61 is also commonly observed. Thus, in recent years a number of tests for the detection of ras mutations have been developed as a means towards clarifying their functional role in tumorigenic pathways, and indeed for their potential utility in the diagnosis and prognosis of cancer.

Primer-mediated restriction fragment length polymorphism (RFLP) analysis was developed as a rapid, non-radioactive method for fast and simple large-scale detection of mutant ras genes (Kahn et al., 1990, Amplifications, 4, 22–26). This method relies upon the polymerase chain reaction (PCR) for amplification of the ras sequences and upon the introduction of restriction endonuclease sites permitting selective restriction cleavage of normal (wild type) ras sequences only, and not of mutant ras sequences. The ras gene primers used for PCR amplification in this process incorporate strategic nucleotide substitutions which serve to create restriction sites overlapping potential activating positions, e.g. positions 12, 13 or 61. The diagnostic restriction site of the target codon is lost in the presence of an activating mutation, thereby permitting detection of the mutant sequences.

However, the detection of ras mutations by this procedure is limited because both mutant and normal sequences are amplified by the PCR step, thereby compromising sensitivity (the number of mutant ras sequences, amongst normal, wild type, DNA may be very low). In more recent years therefore, modifications of the RFLP technique have been developed, whereby mutant ras sequences are selectively amplified (see for example Kahn et al., 1991, Oncogene, 6 1079–1083). This greatly enhances the diagnostic capability of the technique and enables the detection of mutant ras alleles in the presence of up to $10^4$ wild type sequences.

Nonetheless, although the combination of primer-mediated RFLP analysis with selective amplification of mutant sequences permitted a significant advance in ras mutation detection, there is still room for improvement, for example in the sensitivity and specificity of the method, and such improvements are continually being sought. There is therefore a continuing need for improved methods of detecting mutations in ras genes and the present invention is directed towards providing such an improved method.

In particular, we have directed our efforts towards the K-ras gene, and more specifically to the detection of activating mutations at codons 12, 13 and 61 of the K-ras gene, which are believed to be implicated in the development of many common cancers, most notably colo-rectal cancer. Thus, a novel and advantageous primer system has been designed, for use in amplification or RFLP-based ras mutation detection methods, which permit the detection of mutations at codons 12 and/or 13 of the K-ras gene. A further primer system permits detection of mutations at codon 61.

In one aspect, therefore, the present invention provides an oligonucleotide primer sequence for use in in vitro amplification, characterised in that said primer sequence is capable of creating a BstX I restriction site overlapping codon 12 and/or an Xcm I restriction site overlapping codon 13 of the wild-type K-ras oncogene.

The sequence of the wild type human K-ras gene is shown in FIG. 1. The nucleotide sequence of FIG. 1 and the translation products thereof (exons 1, 2, 3, 4A and 4B), also presented in FIG. 1, correspond to SEQ. ID Nos. 1–6.

Mediation of the formation of restriction sites by the primers of the invention is achieved by the provision of a mismatch in the primer at a site, which together with bases present in the wild-type gene sequence, creates the desired restriction site.

A primer sequence according to the invention may thus contain a CCA substitution at the final base of codon 8 and the first two bases of codon 9 of the K-ras gene.

When such a primer is used to direct the in vitro amplification (e.g. by PCR) of a wild-type K-ras sequence, two restriction sites are created, one overlapping the first two, potentially activating, bases of codon 12 (and therefore specific for wild-type codon 12) and the other overlapping the first two, potentially activating bases of codon 13, (and therefore specific for wild-type codon 13). Mutations in the final base positions of codons 12 and 13 do not give rise to changes in the amino acid encoded, and hence are not seen as activating mutations.

When, however, such a primer is used to amplify K-ras sequences mutant at activating positions in codons 12 and 13, a restriction site is not created, since the "correct" bases required to complete the restriction endonuclease recognition site are not present. This therefore enables K-ras sequences containing activating mutations at codons 12 and 13 to be distinguished from wild-type sequences, or more importantly, for the wild-type sequences to be removed, thereby enabling selective amplification of the mutant sequences.

Primers according to the present invention are advantageous in that since restriction sites are created overlapping both codons 12 and 13, mutations at one or both of these sites may readily be detected in the same system. Thus, a single primer may be used to detect the presence or absence of mutations at two sites, thereby considerably simplifying and speeding up the procedure. The utilisation of restriction sites at both loci increases the efficiency of screening and indeed for cancers, e.g. colo-rectal cancer, associated with activations in both codons, the accuracy of the technique.

Different cancers may be associated with different mutations in the K-ras gene, which differ not only in the position of the affected codon, but also in their nature, ie. the actual base substitutions involved. Different combinations of mutations may thus be characteristic of different tumours and identifying mutations at all possible positions could aid in the diagnosis of individual tumours. As mentioned above, codon 61 of the K-ras gene is also commonly affected, and is often associated with different cancers to those caused by mutations in codons 12 and/or 13. It would be helpful therefore to be able to identify mutations at codon 61, in addition to those at codons 12 and 13. Advantageously, therefore, the use of the codon 12/13 primer of the invention is combined with the use of a primer designed to detect mutations at codon 61, ie, by the introduction of restriction sites overlapping codon 61 of the wild type K-ras gene. Thus for example, a primer may be used which creates a Bce 83I restriction site overlapping codon 61.

In a further aspect the invention therefore provides an oligonucleotide primer sequence for use in in vitro amplification, characterised in that said primer sequence is capable of creating a Bce 83I restriction site overlapping codon 61 of the wild-type K-ras oncogene.

Such a primer is advantageous since it covers all possible mutations in codon 61 and thus may be relied upon to give an accurate diagnosis. A representative primer for codon 61 may comprise a sequence corresponding to a C substitution at the second base of codon 60 of the K-ras gene.

Identifying different mutations at different positions may be therapeutically very advantageous since it may permit the targetting of the therapy to the particular cancer concerned. Thus for example, therapies may be directed against the particular mutation, eg. by immunotherapy which stimulates T-cells to kill cells carrying the identified K-ras mutation. Such immunotherapeutic techniques are described in WO92/14756 of Norsk Hydro AS.

Moreover, there is a value in determining not only the codon in which the mutation has occured but also the actual mutation concerned. As mentioned above certain cancers are associated with particular substitutions and furthermore, for some cancers, such as pancreatic cancer, certain mutations give a better prognosis than others. In other words, the prognosis of a cancer may depend on the precise nature of the mutation. Consequently, determination of the sequence following identification of the affected codon is therefore also of clinical value.

In addition to the immunotherapy mentioned above, such targetted therapies, which the present invention may enable to be selected, include the use of ribozymes (JP-A-4235919) and anti-sense RNA (WO92/15680). The product of the ras oncogenes is activated by modification, more specifically by farnesylation, before it exerts its effects. An alternative therapy may therefore involve inhibition of farnesyltransferase enzymes (see for example EP-A-537008).

The length of the primers of the invention is not critical as long as it is sufficient for correct annealing to the template to take place. A length of 20 to 35 bases is suitable for example, and a preferred primer may be e.g. 22 to 30 nucleotides long; and may anneal up to, or just before the potential-activating position. For example for positions 12 and 13 such a primer may comprise the 3' terminal sequence (SEQ. ID NO. 7): 5' . . . CCATGGAGCT 3', where bases CCA correspond to the final base of codon 8, and the first two bases of codon 9 of the K-ras gene.

The primer may be provided with means for immobilisation to a solid support to facilitate subsequent handling and manipulation, for example in the amplification and/or detection steps.

The nature of the means for immobilisation and of the support is a matter of choice. Numerous suitable supports, and methods of attaching nucleotides to them, are well known in the art and widely described in the literature. Thus for example, supports in the form of microtitre wells, tubes, dipsticks, particles, fibres or capillaries may be used, made for example of agarose, cellulose, alginate, teflon, latex or polystyrene. Conveniently, the support may comprise magnetic particles, which permits the ready separation of immobilised material by magnetic aggregation.

The solid support may carry functional groups such as hydroxyl, carboxyl, aldehyde or amino groups for the attachment of nucleotides. These may in general be provided by treating the support to provide a surface coating of a polymer carrying one of such functional groups, eg. polyurethane together with a polyglycol to provide hydroxyl groups, or a cellulose derivative to provide hydroxyl groups, a polymer or copolymer of acrylic acid or methacrylic acid to provide carboxyl groups or an amino alkylated polymer to provide amino groups. U.S. Pat. No. 4,654,267 describes the introduction of many such surface coatings. Alternatively, the support may carry other moieties for attachment, such as avidin or streptavidin (binding to biotin on the nucleotide sequence), DNA binding proteins (eg. the lac I repressor protein binding to a lac operator sequence which may be present in the starting molecule), or antibodies or antibody fragments (binding to haptens eg. digoxigenin on the nucleotide sequence). The streptavidin/biotin binding system is very commonly used in molecular biology, due to the relative ease with which biotin can be incorporated within nucleotide sequences, and indeed the commercial availability of biotin-labelled nucleotides, and thus biotin represents a particularly preferred means for immobilisation.

Where a solid phase amplification procedure is to be employed, the primer of the invention may additionally comprise a further mismatch(es) to create one or more additional restriction sites upstream of the potentially activating positions. Cleavage at such additional restriction sites may be used to detach the nucleotide sequences from the solid support in a quick and simple manner.

A preferred primer sequence according to the invention has the base sequence (SEQ. ID NO. 8):

5' ACTGAATATA AACTTGTGGT CCATGGAGCT 3' and is designated herein primer 5K1.

The CCA is a mismatch corresponding to base 3 of codon 8 and bases 1 and 2 of codon 9 of the K-ras gene and serves, as mentioned above, to introduce restriction sites overlapping activating positions in codons 12 and 13 of the wild-type K-ras gene. Primer 5K1 may, as mentioned above, be modified to enable introduction of a further restriction site upstream of the activating position. For example the modified primer designated 5K1-DraI having the base sequence (SEQ. ID NO. 9)

5' ACTGAATTTA AACTTGTGGT CCATGGAGCT 3' contains an additional mismatch T corresponding to position 2 of codon 3 of the K-ras sequence and serves to introduce a DraI site for cleavage from the support. The primers may be biotinylated to facilitate the use of solid phase techniques.

For codon 61, a preferred primer may have the base sequence (SEQ. ID NO. 10):

5'-TGTCTCTTGGATATTCTCGACACAGCAGcT-3'

The C is a mismatch corresponding to base 2 of codon 60 of the K-ras gene and serves, as mentioned above, to introduce a Bce 83I restriction site overlapping codon 61 of the wild-type K-ras gene.

The cleavage site for endonuclease Bce 83I is (SEQ. ID NO. 11):

NNNNNNNNNNNNNNNNCTCAAG

NNNNNNNNNNNNNNNNGAGTTC

The primers may be modified, for example to create other, different or additional, restriction sites at upstream positions, or to create functionally equivalent analogue primer sequences, capable of functioning, as described above, to mediate the formation of the desired restriction sites.

Primers of the invention are used, as mentioned above, in the in vitro amplification of K-ras sequences in the samples under investigation (i.e. in which activating K-ras mutations are to be detected) using, for example methods as described by Kahn et al., (Supra). Such a sample, which may comprise, for example, blood, serum, urine, expectorate, ascites or other biological fluids, tissue biopsies (which may be fresh or fixed) or even stool samples, optionally appropriately treated using standard techniques to release nucleic acids, will generally contain predominating amounts of wild-type K-ras sequences and minor amounts of mutant, activated, K-ras sequences. Thus for example the nucleic acid isolation technique of our co-pending British Patent Application No. 9323305.4 filed on Nov. 11, 1993 may be used. This involves boiling the sample and allowing it to cool and condense on and within a high surface area solid support.

Any of the in vitro amplification techniques well known and described in the literature may be used. PCR and its modifications will however generally be the principal method of choice. In the case of classical PCR, two primers are of course required, hybridising to opposing strands of the target DNA. The primer of the invention will be used in this regard as the 5', or upstream, amplification primer, and a 3', or downstream, amplification primer may be selected according to choice. In this first amplification step, the choice of 3' primer is not especially critical, as long as it is capable of annealing to the template with sufficient specificity to enable specific amplification. Suitable 3' amplification primers include for example:

5' TTATCTGTAT CAAAGAATGG TCCTGCACCA 3' (3K1) (SEQ. ID NO. 12)

5' TATTAAAACA AGATTTAC 3' (3K3) (SEQ. ID NO. 13)

The sequences and positions of primers 5K1, 3K1 and 3K3 mentioned above, with respect to the wild-type human K-ras gene are shown in FIG. 2, which also shows the respective restriction endonuclease recognition sites which are created. Functionally equivalent modifications of such primer sequences may also be employed.

Modifications of the classical PCR method include, for example, the use of nested primers, in which an additional two "inner" primers are used, which "nest" or hybridise between the first "outer" primer pair. The use of four separate priming events results in increased specificity of the amplification reaction.

Other amplification techniques worthy of mention include Self-sustained Sequence Replication (SSR) and the Q-beta replicase amplification system.

In SSR, primers are used which carry polymerase binding sites permitting the action of reverse transcriptase to amplify target FNA or ssDNA.

In the Q-beta replicase system, an immobilised probe captures one strand of target DNA and is then caused to hybridise with an RNA probe which carries as a template region a tertiary structure known as MDV-1 for an RNA-directed RNA polymerase, normally Q-beta replicase.

As a result of this first amplification step, a population of K-ras fragments is created; amplified wild-type allele fragments contain the primer-mediated restriction sites, whereas mutant allele fragments do not. Subsequently, an aliquot of the amplification mixture is digested with the appropriate restriction enzyme under conventional conditions. The product may then be subjected to direct analysis for detection of the mutant K-ras alleles, for example using the RFLP analysis method of Kahn et al., 1990 (Supra), but more preferably will be subjected to further rounds of amplification for selective "enriched" amplification of the mutant sequences, for example following the method of Kahn et al., 1991 (Supra). In this step, the wild-type sequences have been cleaved and hence are inaccessible to further amplification.

Following this, second, "enriching" amplification step the amplification mixture may be subjected to detection of the mutant K-ras sequence. This may take place by restriction endonuclease digestion and RFLP analysis using the procedure of Kahn et al., 1990 (Supra) or other detection methods. Particular mention may be made in this regard of the detection method known as "detection of immobilised amplified nucleic acids" or DIANA, which is a particularly advantageous technique to be used (see WO90/11369).

In the DIANA detection system, a further PCR amplification step is effected using nested primers, that is a first pair of primers to amplify the target nucleic acid in a first series of cycles, and a second pair of primers hybridising between the first primer pair in a second series of cycles. The inner primers used in the second cycle carry, respectively, means for immobilisation to permit capture of the amplified DNA and a label or means for attachment of a label to permit recognition. The means for immobilisation may, for example, be a hapten such as biotin or digoxigenin while the means for attachment of a signal may include a different hapten or, in a preferred embodiment, a 5'-non-hybridising DNA sequence which is capable of binding to a DNA-binding protein (e.g. the lac operator) carrying an appropriate label. The immobilisation means may also be attached via a 5'-non-hybridising DNA sequence.

As a further check on accuracy, or as the primary detection method, the amplified fragments may be subjected to sequence analysis to verify the mutation, using known sequencing techniques. As mentioned above, this has advantages from a diagnostic point of view, as important differential diagnostic information may be provided.

Conveniently, the final amplification prior to analysis may take place by cycle sequencing. This has the advantage of yielding the base substitution information directly. Such a step would be particularly advantageous for an automated process.

In a further aspect, the present invention thus provides use of an oligonucleotide primer sequence according to the invention as defined above, in an in vitro amplification-based method for detection of activating mutations in codons 12 and/or 13 and/or 61 of the K-ras oncogene.

Viewed from a further aspect, the invention can also be seen to provide a method for detecting activating mutations in codons 12 and/or 13 and/or 61 of the K-ras oncogene, said method comprising subjecting a sample containing the target K-ras DNA to be detected to one or more cycles of in vitro amplification using as an amplification primer, an oligonucleotide primer sequence according to the invention as defined above, followed by restriction endonuclease digestion of wild-type K-ras sequences, using BstX I and/or Xcm I and/or Bce 83I, optionally followed by one or more further cycles of in vitro amplification whereby mutant K-ras sequences containing said activating mutations are enriched, and detecting the said amplified mutant K-ras sequences obtained.

It is preferable, in carrying out the amplification steps according to the invention to introduce one or more additional "control" restriction sites in the amplified fragments. This may be achieved by primer-mediation, using the 3' amplification primer in a manner analogous to that described for the 5' primers of the invention above. Thus, mismatches present in the 3' amplification primer may be used to create the desired control restriction sites (which will correspond to the sites introduced by the 5' primer of the invention). This provides a system to monitor the fidelity of restriction enzyme cleavage.

Thus for example, the following 3' amplification primer may be used (SEQ. ID NO. 14): 5' GAATGGTCCT CACCAGTAA TATGGATATT A 5' (designated herein primer 3K2). The mismatches at positions C and G respectively serve to create BstX I and Xcm restriction sites. Primer 3K2 and its relative position is also shown in FIG. 2.

Where an additional, selective "enriching" amplification step is employed according to the invention, the "modified" internal control 3' primer, will generally only need to be used in the enriching amplification step.

It may also in certain cases be desirable to introduce further modifications to the method, in order for example to enhance specificity and/or sensitivity. Thus it may sometimes occur, that not all of the wild-type K-ras sequences will be digested in the enzyme cleavage step, and that some undigested wild-type sequences may remain. Also, mutated and wild-type strands may reanneal to form heteroduplexes which are not recognised by the restriction enzymes. To enhance specificity of the subsequent "enriching" selective amplification stage, additional amplification and restriction cleavage steps may be employed, using for example nested primers to further enhance specificity. This will be described in more detail in the Examples below, and is illustrated schematically in FIG. 3. It has been shown that by using two restriction endonuclease cutting steps, sensitivity may be improved up to 1:100,000.

Further modifications include as mentioned above the use of solid supports to immobilise the amplification products. In this case, one or both of the amplification primers may be-provided with means for immobilisation e.g. biotin or haptens etc as described above. The use of such a solid phase system is advantageous in that it is cleaner, more efficient and allows the whole process to be carried out in a single tube, thereby minimising losses.

In all the amplification stages, the amplification cycles may be performed using standard conditions which are well known in the art. In order to enhance specificity and sensitivity, it is preferable however to keep the total number of cycles to a minimum and to hybridise the amplification primers at high stringency.

The oligonucleotides according to the invention may be synthesised by known techniques using conventional machine synthesisers such as the Cyclone DNA synthesiser (Biosearch Inc.).

The invention also extends to kits for detection of activating mutations in codons 12 and/or 13 and/or 61 of the K-ras oncogenes, comprising at least one oligonucleotide primer sequence according to the invention. Such kits will normally also contain such additional components as:

(a) for PCR, a polymerase and at least one other oligonucleotide primer; the oligonucleotides both being DNA based and hybridising to opposite strands of the target DNA;

(b) for DIANA, a polymerase and PCR oligonucleotide primers according to the invention provided with means for immobilisation and means for labelling;

(c) for 3SR, a reverse transcriptase and a further DNA oligonucleotides primer, both oligonucleotides being provided with a polymerase binding site;

(d) for Q-beta replicase amplification, an RNA directed RNA polymerase and an RNA probe with a 5'-MDV-1 structure, the capture oligonucleotide being immobilised or permitting immobilisation.

In all the above kits, nucleotide bases will normally be supplied together with appropriate buffers.

The following Examples are given by way of illustration only with reference to the following Figures.

BRIEF DESCRIPTION OF THE DRAWINGS

FIG. 1 shows the nucleotide and corresponding amino acid sequence of the human cellular proto-oncogene K-ras (c-ki-ras2). Mutating hot spots are underlined;

FIG. 2 shows the sequences of the primers used in the Examples and their positions with respect to the wild-type K-ras gene. The cleavage sites of the restriction endonucleases BstXI and XcmI are also shown;

EXAMPLE 1

Figure 3A:
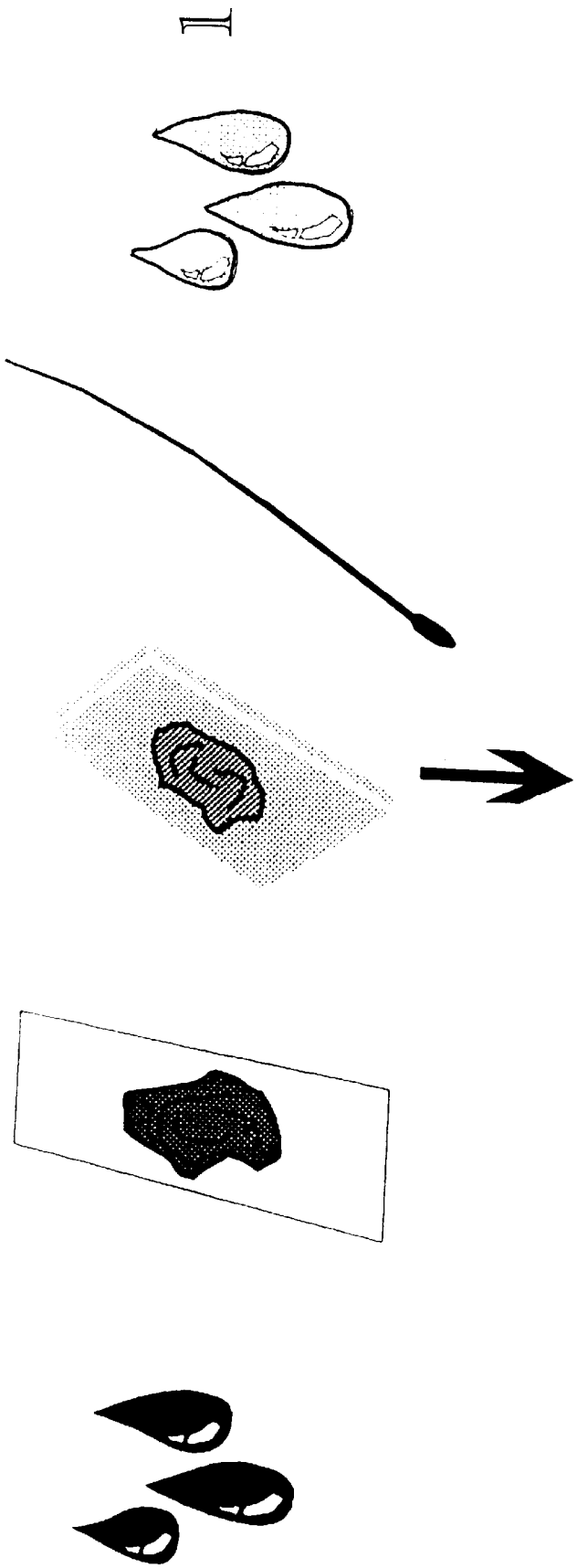
FIG. 3 shows a schematic representation of the steps involved in carrying out the K-ras mutation detection procedure of the present invention as described in Examples 1 and 2.
Figure 3B:
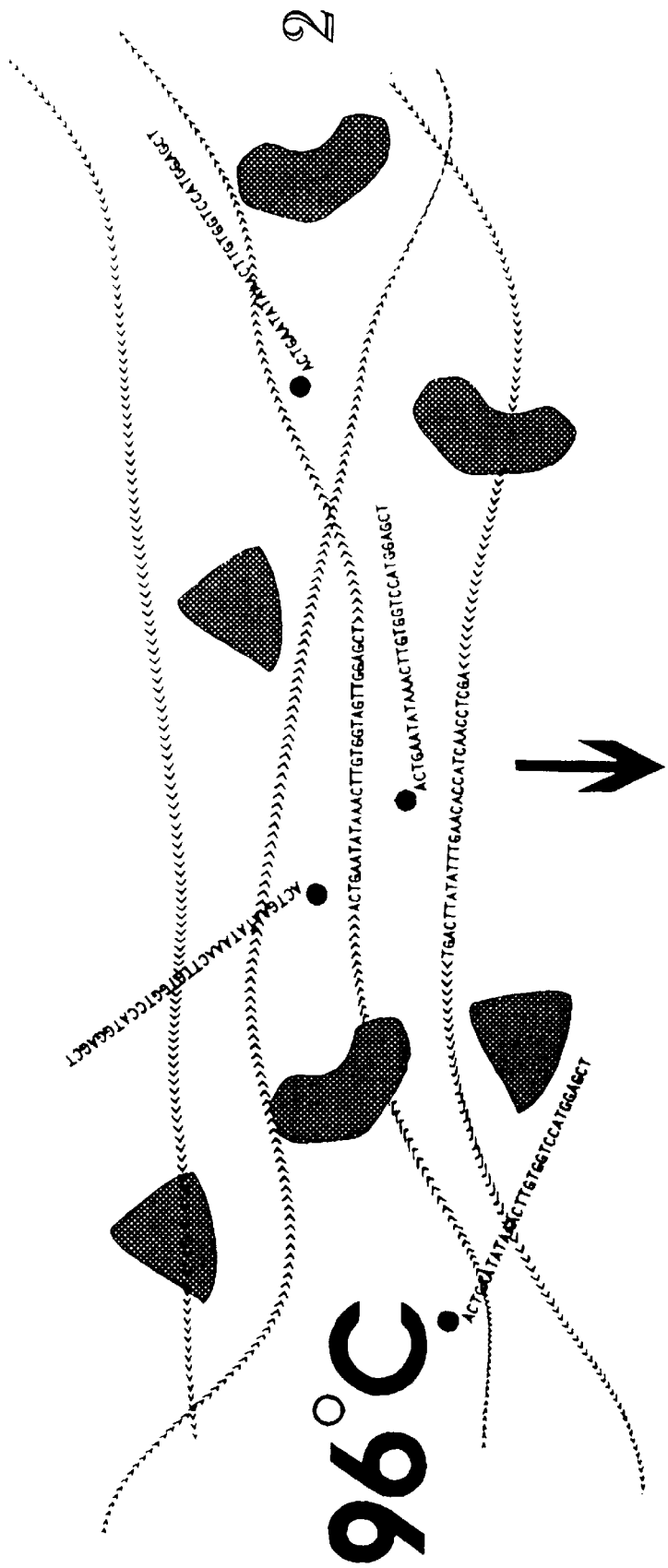
Figure 3C:
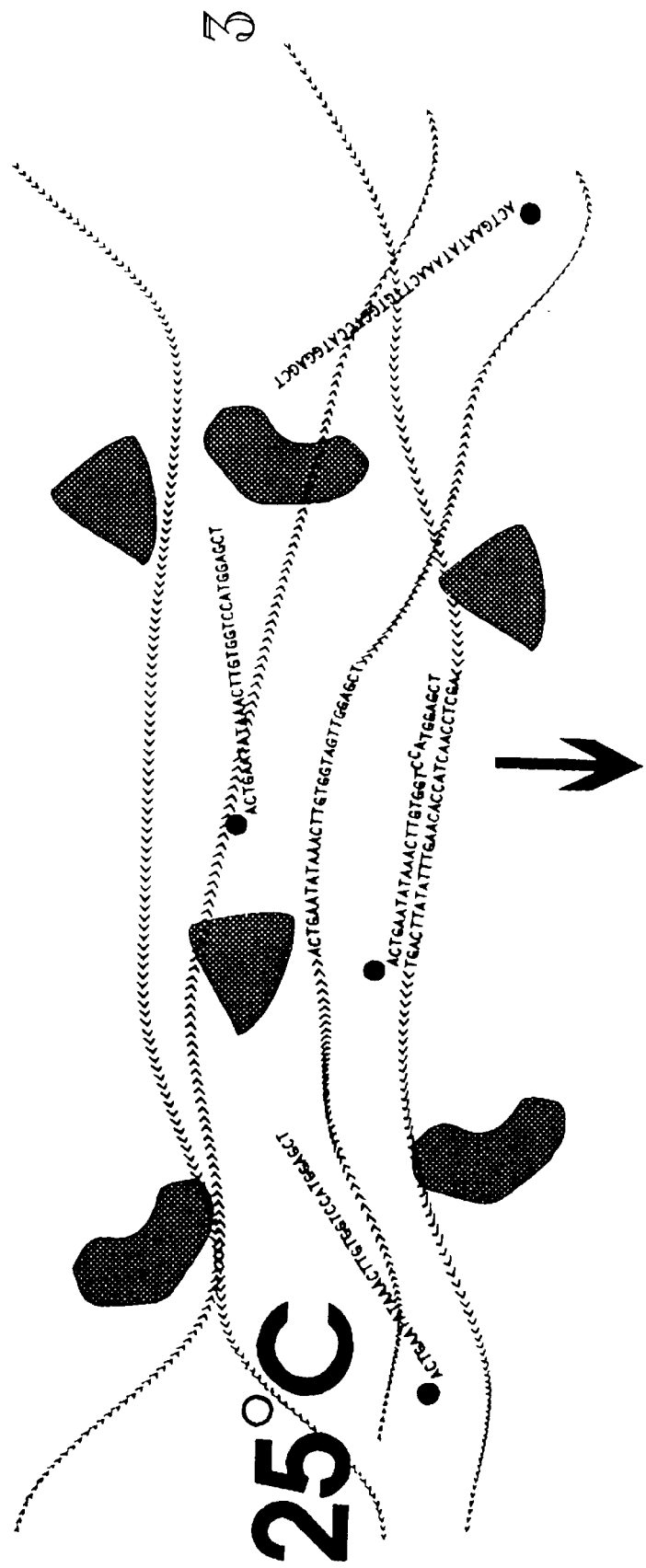
Figure 3D:
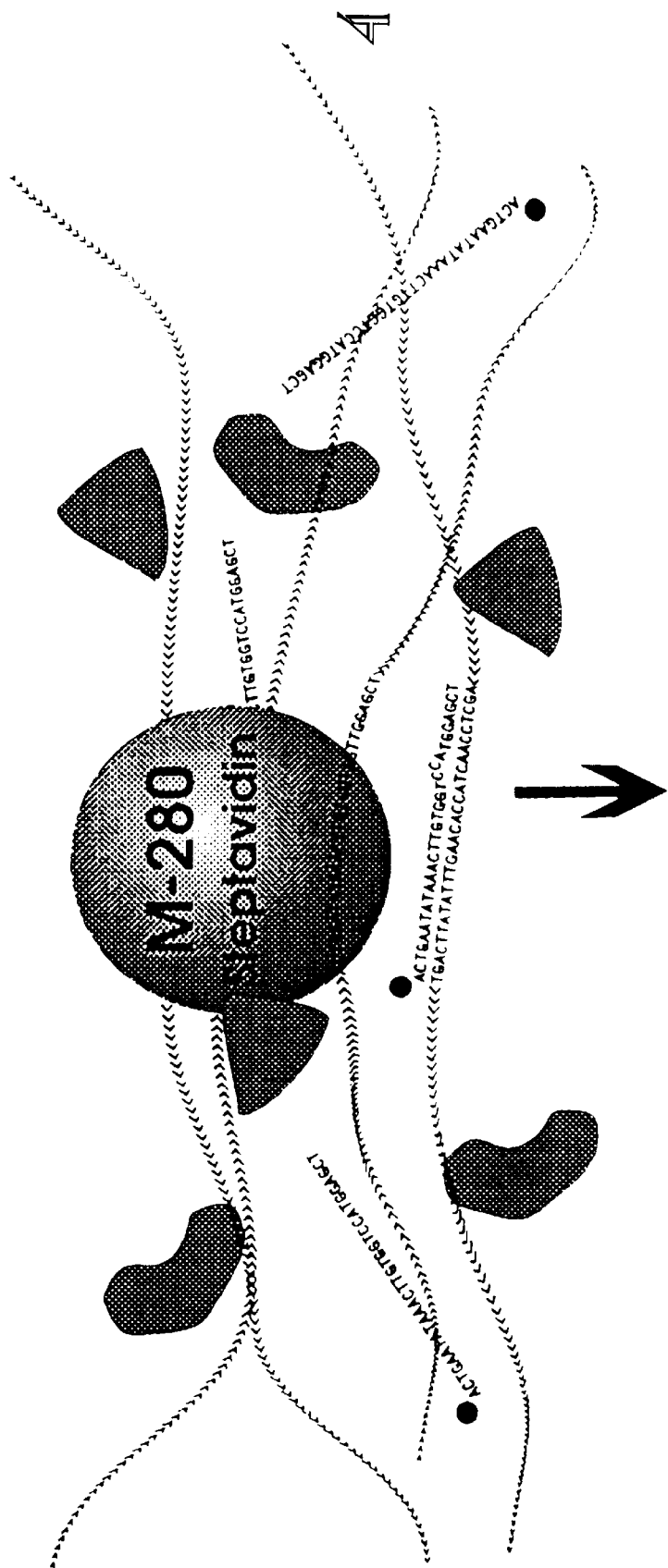
Figure 3E:
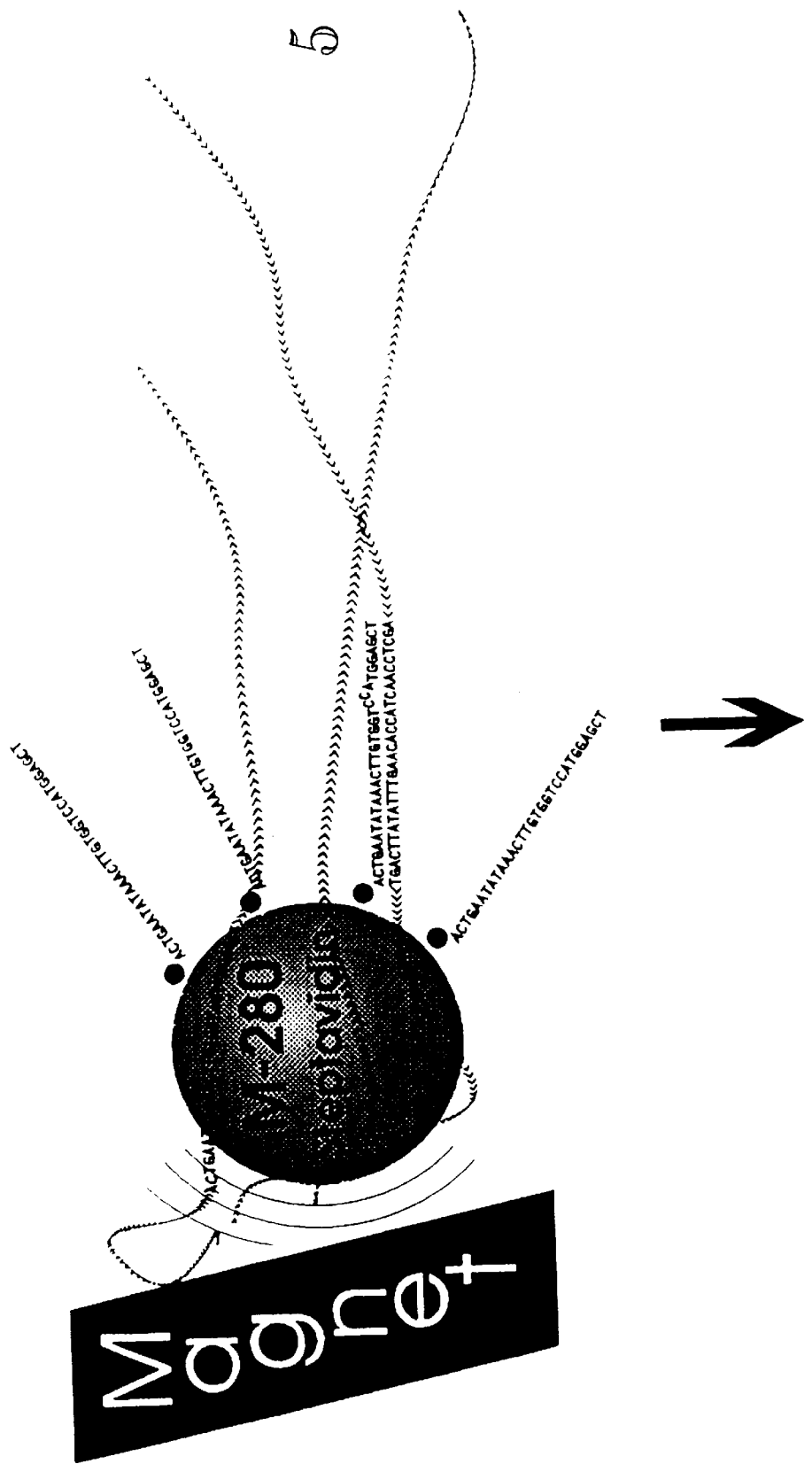
Figure 3G:
Figure 3L:
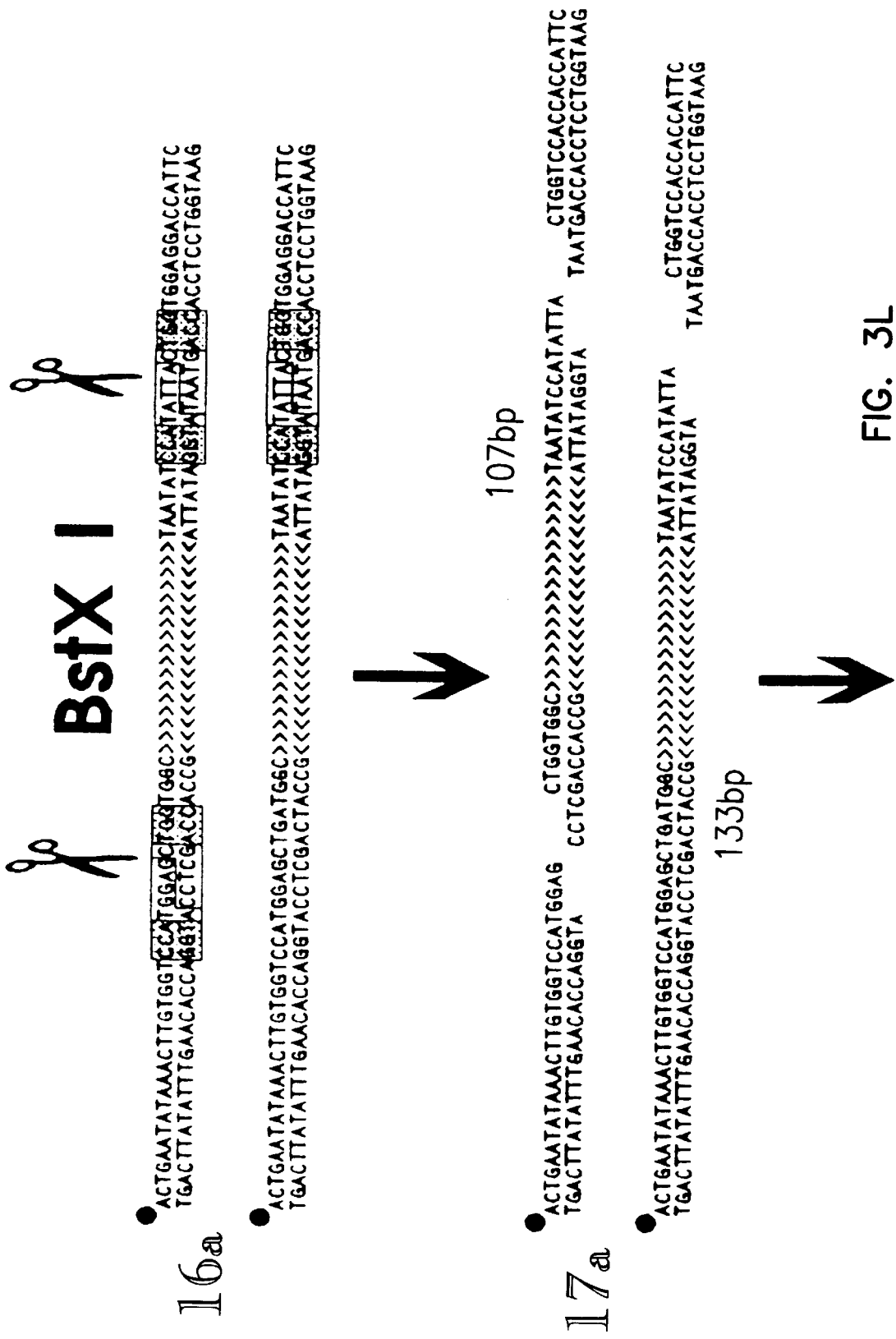
Figure 3M:
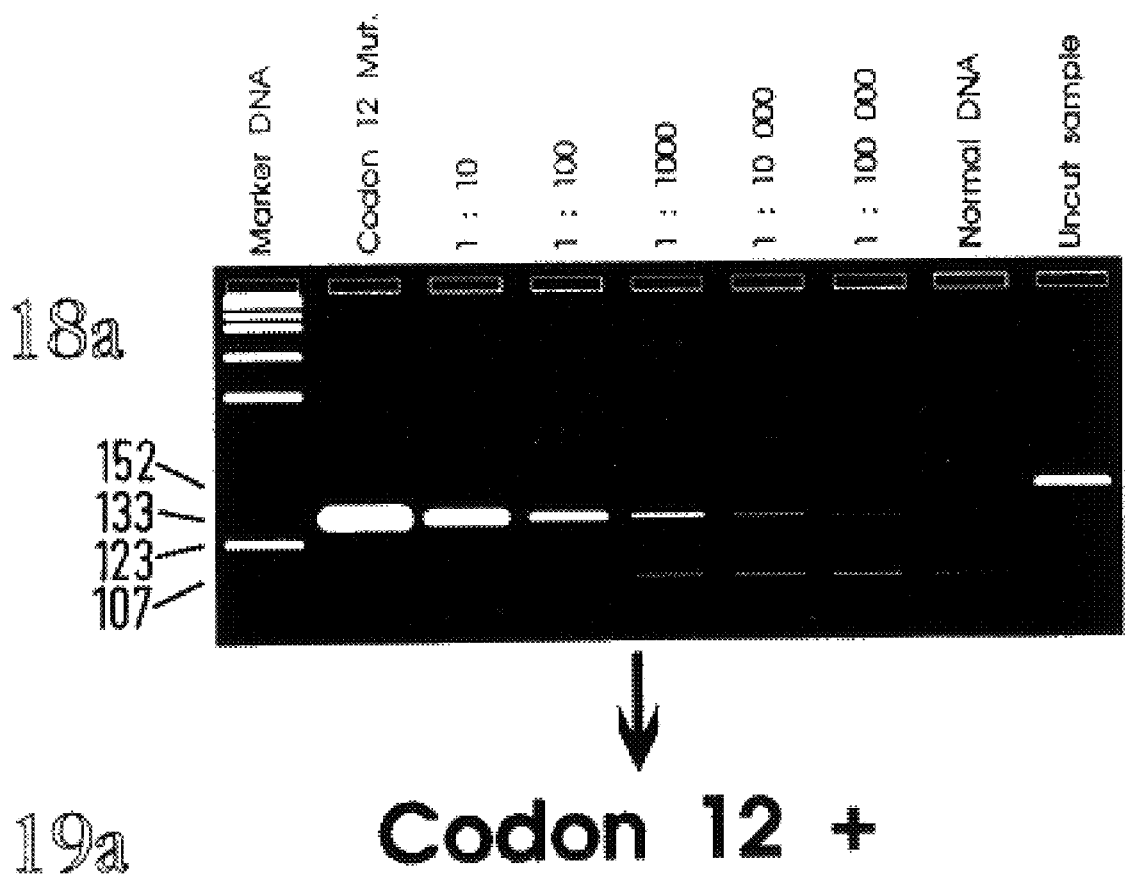
Figure 3S:
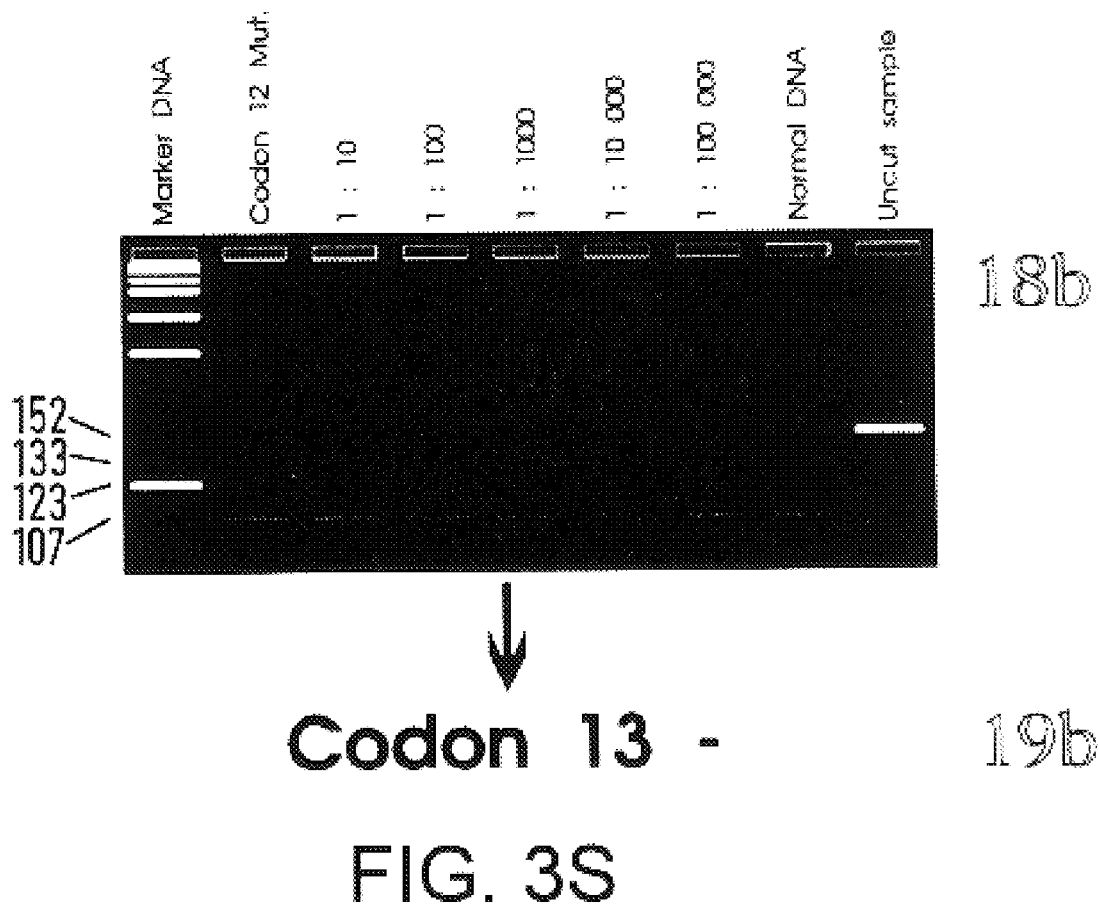

This sets out a general description of the performance of the method of the invention, to detect mutation in codon 12 of the K-ras gene, using a primer according to the invention, and is illustrated schematically in FIG. 3.

1: DNA may be isolated from different types of sample (expectorate, faeces, fixed tissue, urine, ascites, blood, etc.).

2: A small amount of sample is mixed in a salt-buffer containing a biotinylated oligonucleotide probe for the gene under study. The tube is then heated and vortexed to release and denature DNA-strands. In this example we have a mix of normal DNA (in excess) and DNA with a point mutation (G→A) in the second base of codon 12 of the K-ras gene.

3: The solution is cooled, and the probe binds to the denatured DNA.

4: Magnetic streptavidin coated beads are added to solution, DNA binds to the beads both unspecifically and by the streptavidin-biotin binding (where there is a biotinylated primer).

5: Beads with bound DNA are isolated from contaminating debris and inhibitors by magnetic separation, and added as template to a PCR amplification.

6: Amplification is performed using a modified 5' primer (5K1) and an ordinary 3' primer (3K1).

7: An amplification product containing the induced modifications is produced. This product is then used in two parallel procedures which differ only in the type of endonuclease used.

8a: The amplification product is incubated with a endonuclease (BstX 1) specific for the sequence CCANNNNNNTGG (N=G, T, A or C)(SEQ. ID NO. 15).

8b: The amplification product is incubated with a endonuclease (Xcm 1) specific for the sequence CCANNNNNNNNNTGG (N=G, T, A or C)(SEQ. ID NO. 16).

9a: BstX 1 cuts the product with a normal codon 12 but not the mutated product. For several reasons there may not be a complete cutting of the normal sequence.

9b: Xcm 1 cuts both the normal and mutated product since there is no mutation in codon 13. For several reasons there may not be a complete cutting of the product.

10a/b–13a/b: The digested product is used as template in an amplification identical to step 6. The mutated product is preferentially amplified because most of the normal product has been cut by the enzymes. The endonuclease digestion is repeated to increase sensitivity.

14a/b: The digested product is used as template in an amplification using a biotinylated 5' primer (5K1-bio) and a modified 3' primer (3K2) containing both of the two restriction sites.

15a/b: An amplification product containing the modifications is produced.

16a/b: The products are digested with their respective endonucleases.

17a: The mutated product is cut only at the control site introduced by 3K2, while the normal product is cut at both sites.

17b: All of the product is cut at both sites since there is no mutation in codon 13.

18a: The figure illustrates how different ratios of mutated vs. normal in the sample will look on an electrophoresis of the digested end-product. A 133 bp band indicate mutation, normal products result in a 107 bp band and undigested products are seen as a band at 152 bp.

18b: All of the product from a sample with mutation in codon 12 are cut by Xcm 1. This enzyme is specific for the amplification product carrying wild type codon 13.

19a/b: From the electrophoresis we can determine if there is a mutation and in what codon. To identify the type of base substitution, the biotinylated strand of the product is sequenced by solid-phase sequencing.

EXAMPLE 2

Detection of K-ras Mutation in Formalin-fixed Paraffin-embedded Needle-biopsy from Pancreatic Cancer This Example was performed using the general procedure set out in EXAMPLE 1.

Sample and Controls

1: Colon-cancer cell-line SW480 with known K-ras codon 12 mutation (GTT) and no normal allele.
2: Formalin-fixed paraffin-embedded tissue from normal colonic mucosa.
3: Formalin-fixed paraffin-embedded needle-biopsy (1 mm×10 mm) from pancreatic cancer.
4: Distilled water (control without DNA).

DNA Preparation

From Cell-line

DNA from SW480 is extracted (phenol/chloroform) and quantified using standard methods. 1 $\mu$g of this DNA is used as positive control of mutation.

From Paraffin Blocks

Two 5 $\mu$m thick slides are cut of from each of the blocks. The microtom blade is washed twice in xylol and once in ethanol before each cutting.

The slides are added to 500 $\mu$l micro-centrifuge tubes containing:

Bind & Wash buffer (Dynal, Norway), 400 $\mu$l:
Tris-HCl 10 mM, pH 7.5
EDTA 1 mM
NaCl 2.0 M
5K1-Bio 3 pmol The tubes are incubated at 94° C. for 5–10 minutes in a thermal cycler, and the contents mixed twice on a vortex-mixer for 20 seconds during this incubation.

When the tubes has been cooled to ambient temperature (for about 3 minutes), the liquid phase is pipetted off and mixed with 20 $\mu$g of streptavidin coated paramagnetic beads (Dynabeads© M-280 streptavidin, Dynal, Norway).

The mixture is left at ambient temperature for 15 minutes.

The beads are isolated by magnetic separation (Dynal MPC©-E, Dynal, Norway), and used as template to the amplification reaction.

Amplification

Three (A1, A2 and B) serial PCRs with two intermediate destructions of non-mutated alleles by a specific endonuclease (in this case BstX 1) are performed. To avoid miss-priming a "hot-start" PCR-method is performed (i.e. the amplification reaction is not started until the reaction-mix reaches a certain temperature). This is accomplished by dividing essential reagents by a layer of wax (Para Clean II (melting range 55–57° C.), Klinipath, Zevenaar, Netherlands) which melts at higher temperatures.

PCR amplifications was performed in a total volume of 50 $\mu$l:

dNTP 0.025 mM each
potassium chloride 50 mM
magnesium chloride 1.5 mM
Tris-HCl 10 mM pH 8.4
gelatin 0.01%
primers 0.2 $\mu$M each
Taq polymerase 2.5 units (AmpliTaq® DNA Polymerase, Perkin Elmer, Conn., USA)

The wax (17 $\mu$l) divides the reaction-mix in two compartments of equal volume. Only the lower compartment contains dNTP and primers, and polymerase and template are added above the wax-layer.

Thermal-cycling is performed in 200 $\mu$l MicroAmp™ reaction tubes with the GenAmp™ PCR System 9600 (Perkin-Elmer, Conn., USA):

One cycle consists of 30 sec denaturation at 94° C., 1 min. annealing at 50° C. and 2 min. elongation at 72° C. After the last cycle the tubes are kept for 8 min. at the elongation temperature.

Destruction of Non-mutated Amplification Product

5 $\mu$l of the amplification product is digested with restriction endonuclease BstX 1 (New England Biolabs, Mass., USA) in a total volume of 20 $\mu$l at conditions recommended by the supplier.

5 $\mu$l of the digested solution is used as template in the proceeding amplification step.

Amplification/Digestion Procedure

The first PCR (A1) consists of 15 cycles with 5K1 and 3K1 as primers and genomic DNA as template.

The amplification product is then digested with BstX 1 (A samples, B samples follow the same procedure but without the enzyme (BstX 1)) to destroy product that is not mutated in codon 12 for further amplification.

The digested product is used as template for 15 more cycles with 5K1 and 3K1 as primers (PCR A2).

A second BstX 1 digestion (A samples, B samples follow the same procedure but without the enzyme (BstX 1)) is performed to increase sensitivity.

The digested product is used as template for 35 cycles (PCR B) with a biotinylated primer (5K1-Bio) and a primer introducing control restriction-sites (3K2).

RFLP Analysis

Ten $\mu$l of the amplification product of PCR B is digested with BstX 1 in a total volume of 20 $\mu$l.

Figure 4:
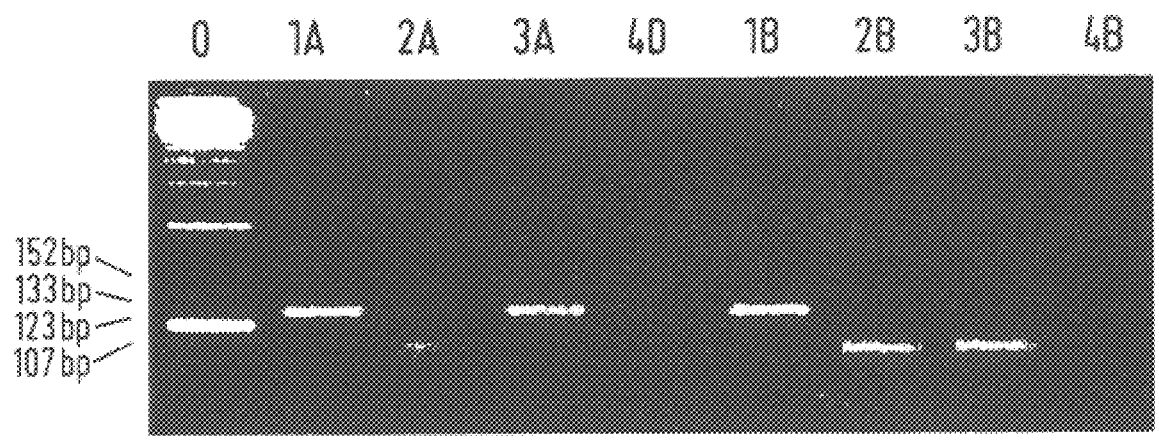
FIG. 4 shows the results of electrophoresis of the amplification products of Example 2 in a 4% agarose gel containing ethidium bromide and analysed under UV light.

The digested amplification product is subjected to electrophoresis in a 4% agarose gel containing ethydium bromide and analyzed in UV-light (FIG. 4).

Mutated product is identified as a 133 bp band. Non-mutated samples show up as 107 bp bands if they are not completely eliminated by the procedure. Undigested product is found as 152 bp fragments.

Solid-phase Sequencing

The oligonucleotide sequence of the amplification product is identified by solid-phase sequencing using streptavidin coated paramagnetic beads (Dynabeads© M-280 streptavidin, Dynal, Norway) as solid-support.

The biotinylated strand of the amplification product (PCR B) is isolated as described by the supplier of the beads (Technical handbook, Molecular Biology, 1st Ed., Dynal, Norway).

The sequencing reaction is performed as described by the supplier of the kit (Sequenase®, Version 2.0, United States Biochemical, Ohio, USA) with 3K3 as the sequencing primer.

Figure 5:
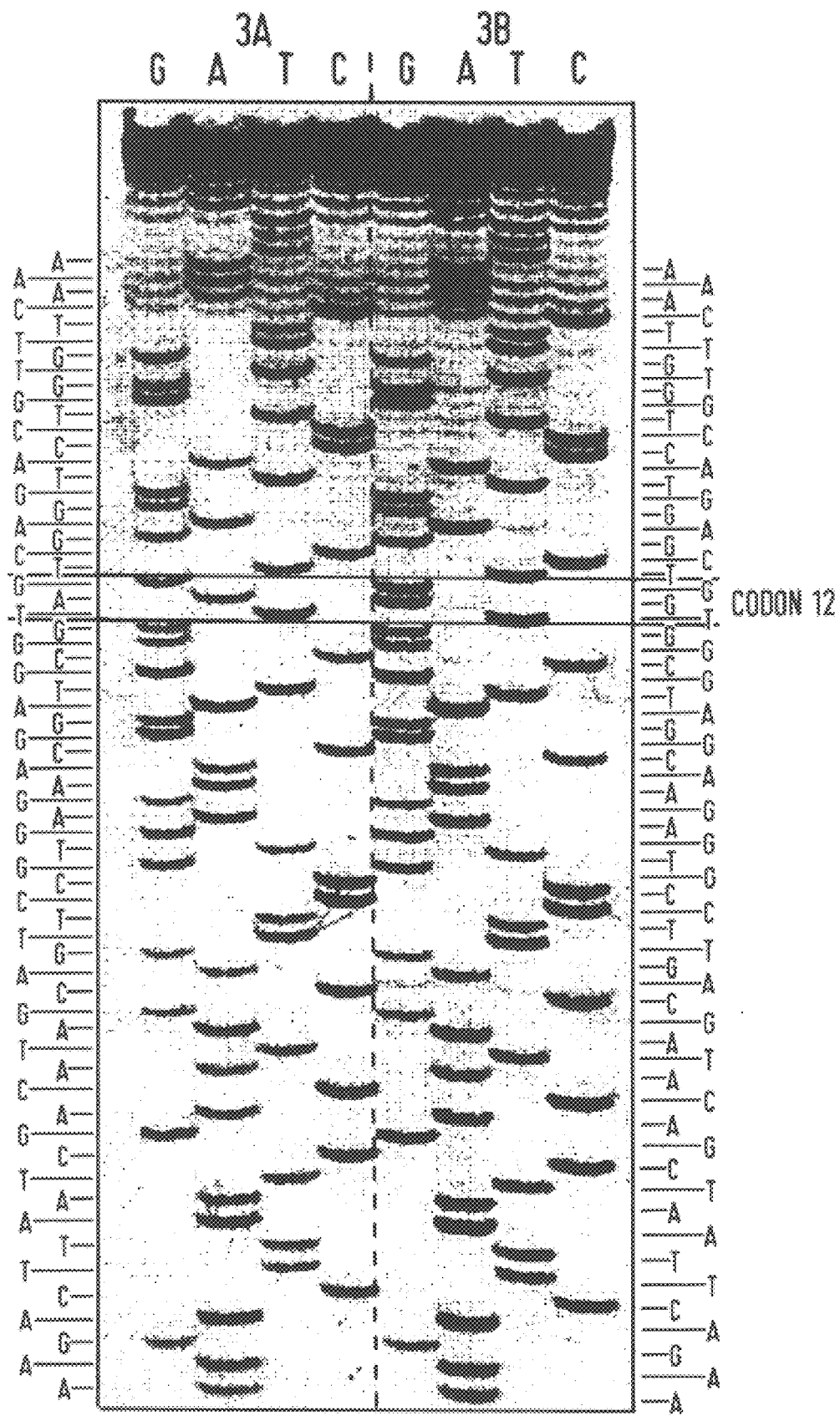
FIG. 5 shows the results of sequence analysis of the products of Example 2, 6% polyacrylamide gel. Panel 3A shows the sequence of the mutated products obtained from the needle biopsy (sample 3A); Panel 3B shows the sequence obtained from the same sample using the same procedure but without adding endonuclease (BstXI) in the two intermediate destructions of non-mutated amplification product.

The sequence of the mutated product obtained from the needle-biopsy (sample 3A) is shown in FIG. 5. The right sequence (3B) is obtained from the same sample using the same procedure, but without adding endonuclease (BstX 1) in the two intermediate destructions of non-mutated amplification product. This illustrates how a weak non-informative mutated band is enhanced, and the background of the normal allele is removed.

An identical procedure using endonuclease Xcm 1 instead of BstX 1 allows detection of mutations in codon 13.

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 3918 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Homo sapiens (ix) FEATURE:
      (A) NAME/KEY: exon
      (B) LOCATION:825..947

(ix) FEATURE:
      (A) NAME/KEY: exon
      (B) LOCATION:1388..1567

(ix) FEATURE:
      (A) NAME/KEY: exon
      (B) LOCATION:2118..2278

(ix) FEATURE:
      (A) NAME/KEY: exon
      (B) LOCATION:3034..3158

(ix) FEATURE:
      (A) NAME/KEY: exon
      (B) LOCATION:3459..3616

(xi) SEQUENCE DESCRIPTION: SEQ ID NO: 1:

```
CCGCGGTCCG GTCCCGCTCC GGGTCAGAAT TGGCGGCTGC GGGGACAGCC TTGCGGCTAG      60

GCAGGGGGCG GGCCGCCGCG TGGGTCCGGC AGTCCCTCCT CCCGCCAAGG CGCCGCCCAG     120

ACCCGCTCTC CAGCCGGCCC GGCTCGCCAC CCTAGACCCC CCCAGCCACC CCTTCCTCCG     180

CCGGCCCGGC CCCCGCTCCT CCCCCGCCGG CCCGGCCCGG CCCCCTCCTT CTCCCCGCCG     240

GCGCTCGCTG CCTCCCCCTC TTCCCTCTTC CCACACCGCC CTCAGCCGCT CCCTCTCGTA     300

CGCCCGTCTG AAGAAGAATC GAGCGCGGAA CGCATCGATA GCTCTGCCCT CTGCGGCCGC     360

CCGGCCCCGA ACTCATCGGT GTGCTCGGAG CTCGATTTTC CTAGGCGGCG GCCGCGGCGG     420

CGGAGGCAGC AGCGGCGGCG GCAGTGGCGG CGGCGAAGGT GGCGGCGGCT CGGCCAGTAC     480

TCCCGGCCCC CGCCATTTCG GACTGGGAGC GAGCGCGGCG CAGGCACTGA AGGCGGCGGC     540

GGGGCCAGAG GCTCAGCGGC TCCCAGGTGC GGGAGAGAGG TACGGAGCGG ACCACCCCTC     600

CTGGGCCCCT GCCCGGGTCC CGACCCTCTT TGCCGGCGCC GGGCGGGGCC GGCGGCGAGT     660
```

```
GAATGAATTA GGGGTCCCCG GAGGGGCGGG TGGGGGCGC GGGCGCGGGG TCGGGGCGGG      720

CTGGGTGAGA GGGGTCTGCA GGTACTGGTG GAGTATTTGA TAGTGTATTA ACCTTATGTG      780

TGACATGTTC TAATATAGTC ACATTTTCAT TATTTTTATT ATAAGGCCTG CTGAAAATGA      840

CTGAATATAA ACTTGTGGTA GTTGGAGCTG GTGGCGTAGG CAAGAGTGCC TTGACGATAC      900

AGCTAATTCA GAATCATTTT GTGGACGAAT ATGATCCAAC AATAGAGGTA AATCTTGTTT      960

TAATATGCAT ATTACTGGTG CAGGACCATT CTTTGATACA GATAAAGGTT TCTCTGACC      1020

TTTTCATGAG TATCACCATT TTACATTCCC ACCAGCAATG CACAAAGATT TCAGTGTCT      1080

TATCCTTGCT AACACTTATT TTCCATTTTT TGAGTTTTTT TGTTTTGTTT TTTTAATAA      1140

AGCCAATCCT AATGGGTATG TGGTAGCATC TCATGGTTTT GATTTTATTT TCCTGACTA      1200

TGATGATGTT GAGCATCTTT TCAGGTGCTT AGTGGCCATT TGTCCGTCAT CTTTGGAGC      1260

GGAACAATGT CTTTTCAAGT CCTTTGCCCA TTTTTAAATT GAATTTTTTG TTGTTGAGT      1320

GTATATAACA CCTTTTTTGA AGTAAAAGGT GCACTGTAAT AATCCAGACT GTGTTTCTC      1380

CTTCTCAGGA TTCCTACAGG AAGCAAGTAG TAATTGATGG AGAAACCTGT CTCTTGGAT      1440

TTCTCGACAC AGCAGGTCAA GAGGAGTACA GTGCAATGAG GACCAGTAC ATGAGGACT       1500

GGGAGGGCTT TCTTTGTGTA TTTGCCATAA ATAATACTAA ATCATTTGAA GATATTCAC      1560

ATTATAGGTG GGTTTAAATT GAATATAATA AGCTGACATT AAGGAGTAAT TATAGTTTT      1620

ATTTTTTGAG TCTTTGCTAA TGCCATGCAT ATAATATTTA ATAAAAATTT TTAAATAAT      1680

TTTATGAGGT AGGTAATATC CCTGTTTTAT AAATGAAGTT CTTGGGGGAT TAGAGCAGT      1740

GAGTAACTTG CTCCAGACTG CATCGGTAGT GGTGGTGCTG GGATTGAAAC CTAGGCCTG      1800

TTGACTCCAC AGCCTTCTGT TCTAGAATTT TTCAGTAGTT TCTGTTTTAC TATTATGAT      1860

TACCTGCATA TTAACCTATT AGGTTATAGT TTTACTATAC TTCTAGGTAT TTGATCTTT      1920

GAGAGAGATA CAAGGTTTCT GTTTAAAAAG GTAAAGAAAC AAAATAACTA GTAGAAGAA      1980

GAAGGAAAAT TTGGTGTAGT GGAAACTAGG AATTACATTG TTTTCTTTCA GCCAAATTT      2040

ATGACAAAAG TTGTGGACAG GTTTTGAAAG ATATTTGTGT TACTAATGAC TGTGCTATA      2100

CTTTTTTTTC TTTCCCAGAG AACAAATTAA AAGAGTTAAG GACTCTGAAG ATGTACCTA      2160

GGTCCTAGTA GGAAATAAAT GTGATTTGCC TTCTAGAACA GTAGACACAA AACAGGCTC      2220

GGACTTAGCA AGAAGTTATG GAATTCCTTT TATTGAAACA TCAGCAAAGA CAAGACAGG      2280

AAGTAACACT GAAATAAATA CAGATCTGTT TTCTGCAAAA TCATAACTGT TATGTCATT      2340

AATATATCAG TTTTTCTCTC AATTATGCTA TACTAGGAAA TAAAACAATA TTTAGTAAA      2400

GTTTTTGTCT CTTGAGAGGG CATTGCTTCT TAATCACAGA AGACCCAGTC TCAGCTTCA      2460

TTGTATACCC TGGAAATAGA CTGAAAGGTG TTAAAATTTA AAATAAAACT CAAGGTTCC      2520

GTTTCTTGAC TCACCTTTGA GATTCTTTTA TGTTTTTGTT GTTTTTTAAC AAAGGTTTC      2580

CGTCCATATT TTACCATTTT TCTTCTCATT CTCCCCTGGA GGAGGGTGTG GGAATCGAT      2640

GTATATAAAT CACTTTTTTC CTAAGTCAAA GAAGTAATTT AAAGCTAACT TCAGTTTAG      2700

CTTTAATTCC AGGACTAGCA AACTAAAATG GTTGCATTAA TTGACAAACA GATGCTAAT      2760

CCTGTGTTTA GGCTTGTCAT AATCTCTCCT AATTCCTAAT TTAAAATTT TAAAATTTA       2820

TTCCATTAGA AAACAAAACT GACTTTTAAG AACAAACCAG GATTCTAGCC CATATTTTA      2880

AACTGCATCC TCAGTTTTAT TCAAACAGTC TGATGTCTGT TTAAAAAAAA AAAAATCTC      2940

AGCTCATAAT CTCAAACTTC TTGCACATGG CTTTCCCAGT AAATTACTCT TACCAATGC      3000

ACAGACTTTA AAGAAGTTGT GTTTTACAAT GCAGAGAGTG GAGGATGCTT TTTATACAT      3060
```

-continued

```
GGTGAGAGAG ATCCGACAAT ACAGATTGAA AAAAATCAGC AAAGAAGAAA AGACTCCTG         3120

CTGTGTGAAA ATTAAAAAAT GCATTATAAT GTAATCTGGT AAGTTTAAGT TCAGCACAT         3180

AATTTTGGCA GAAAGCAGAT GTCTTTTAAA GGTAACAAGG TGGCAACCAC TTTAGAACT         3240

CTTAGGTGTA GTATTCTAAC TTGAAGTATT AAAAGATAAA AAACTTGTTT CCATAATTA         3300

TGAATTCTAA AAGTCCTAAT ATATGTAATA TATATTCAGT TGCCTGAAGA GAAACATAA         3360

GAATCCTTTC TTAATATTTT TTCCATTAAT GAAATTTGTT ACCTGTACAC ATGAAGCCA         3420

CGTATATATT CACATTTTAA TACTTTTTAT GTATTTCAGG GTGTTGATGA TGCCTTCTA         3480

ACATTAGTTC GAGAAATTCG AAAACATAAA GAAAAGATGA GCAAAGATGG TAAAAAGAA         3540

AAAAAGAAGT CAAAGACAAA GTGTGTAATT ATGTAAATAC AATTTGTACT TTTTTCTTA         3600

GGCATACTAG TACAAGTGGT AATTTTTGTA CATTACACTA AATTATTAGC ATTTGTTTT         3660

GCATTACCTA ATTTTTTTCC TGCTCCATGC AGACTGTTAG CTTTTACCTT AAATGCTTA         3720

TTTAAAATGA CAGTGGAAGT TTTTTTTTCC TCGAAGTGCC AGTATTCCCA GAGTTTTGG         3780

TTTTGAACTA GCAATGCCTG TGAAAAAGAA ACTGAATACC TAAGATTTCT GTCTTGGGG         3840

TTTTGGTGCA TGCAGTTGAT TACTTCTTAT TTTTCTTACC AAGTGTGAAT GTTGGTGTG         3900

AACAAATTAA TGAAGCTT                                                     3918
```

(2) INFORMATION FOR SEQ ID NO: 2:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Homo sapiens (xi) SEQUENCE DESCRIPTION: SEQ ID NO: 2:

```
Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
            20                  25                  30

Asp Pro Thr Ile Glu
        35
```

(2) INFORMATION FOR SEQ ID NO: 3:

(i) SEQUENCE CHARACTERISTICS:
        (A) LENGTH: 59 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Homo sapiens (xi) SEQUENCE DESCRIPTION: SEQ ID NO: 3:

```
Asp Ser Tyr Arg Lys Gln Val Val Ile Asp Gly Glu Thr Cys Leu Leu
 1               5                  10                  15

Asp Ile Leu Asp Thr Ala Gly Gln Glu Glu Tyr Ser Ala Met Arg Asp
            20                  25                  30

Gln Tyr Met Arg Thr Gly Glu Gly Phe Leu Cys Val Phe Ala Ile Asn
```

```
                35                  40                  45
Asn Thr Lys Ser Phe Glu Asp Ile His His Tyr
 50                  55
```

(2) INFORMATION FOR SEQ ID NO: 4:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 4:

```
Glu Gln Ile Lys Arg Val Lys Asp Ser Glu Asp Val Pro Met Val Leu
 1               5                  10                  15
Val Gly Asn Lys Cys Asp Leu Pro Ser Arg Thr Val Asp Thr Lys Gln
                20                  25                  30
Ala Gln Asp Leu Ala Arg Ser Tyr Gly Ile Pro Phe Ile Gly Thr Ser
                35                  40                  45
Ala Lys Thr Arg Gln
 50
```

(2) INFORMATION FOR SEQ ID NO: 5:

(i) SEQUENCE CHARACTERISTICS:
        (A) LENGTH: 39 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

```
Arg Val Glu Asp Ala Phe Tyr Thr Leu Val Arg Glu Ile Arg Gln Tyr
 1               5                  10                  15
Arg Leu Lys Lys Ile Ser Lys Glu Lys Thr Pro Gly Cys Val Lys
                20                  25                  30
Ile Lys Lys Cys Ile Ile Met
                35
```

(2) INFORMATION FOR SEQ ID NO: 6:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 6:

```
Gly Val Asp Asp Ala Phe Tyr Thr Leu Val Arg Glu Ile Arg Lys His
 1               5                  10                  15
Lys Glu Lys Met Ser Lys Asp Gly Lys Lys Lys Lys Lys Ser Lys
                20                  25                  30
Thr Lys Cys Val Ile Met
                35
```

(2) INFORMATION FOR SEQ ID NO: 7:

(i) SEQUENCE CHARACTERISTICS:
        (A) LENGTH: 10 base pairs

-continued (B) TYPE: nucleic acid
        (C) STRANDEDNESS: single
        (D) TOPOLOGY: linear (ii) MOLECULE TYPE: other nucleic acid
        (A) DESCRIPTION:  /desc = "oligonucleotide"

(xi) SEQUENCE DESCRIPTION: SEQ ID NO: 7:

CCATGGAGCT                                                                  10

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "oligonucleotide primer"

(xi) SEQUENCE DESCRIPTION: SEQ ID NO: 8:

ACTGAATATA AACTTGTGGT CCATGGAGCT                                             30

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "oligonucleotide primer"

(xi) SEQUENCE DESCRIPTION: SEQ ID NO: 9:

ACTGAATTTA AACTTGTGGT CCATGGAGCT                                             30

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "oligonucleotide primer"

(xi) SEQUENCE DESCRIPTION: SEQ ID NO: 10:

TGTCTCTTGG ATATTCTCGA CACAGCAGCT                                             30

(2) INFORMATION FOR SEQ ID NO: 11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "oligonucleotide - cleavage
            site for Bce 83I"

(xi) SEQUENCE DESCRIPTION: SEQ ID NO: 11:

NNNNNNNNNN NNNNNNCTCA AG                                                    22

(2) INFORMATION FOR SEQ ID NO: 12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide primer"

(xi) SEQUENCE DESCRIPTION: SEQ ID NO: 12:

TTATCTGTAT CAAAGAATGG TCCTGCACCA                                               30

(2) INFORMATION FOR SEQ ID NO: 13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide primer"

(xi) SEQUENCE DESCRIPTION: SEQ ID NO: 13:

TATTAAAACA AGATTTAC                                                            18

(2) INFORMATION FOR SEQ ID NO: 14:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide primer"

(xi) SEQUENCE DESCRIPTION: SEQ ID NO: 14:

GAATGGTCCT CCACCAGTAA TATGGATATT A                                             31

(2) INFORMATION FOR SEQ ID NO: 15:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide - cleavage
                site for Bst X1"

(xi) SEQUENCE DESCRIPTION: SEQ ID NO: 15:

CCANNNNNNT GG                                                                  12

(2) INFORMATION FOR SEQ ID NO: 16:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "oligonucleotide - cleavage
                site for Xcm 1"

(xi) SEQUENCE DESCRIPTION: SEQ ID NO: 16:

CCANNNNNNN NNTGG                                                               15

We claim:

1. An oligonucleotide primer comprising a sequence for use in in vitro amplification, characterised in that said primer is capable of creating a BstXI restriction site overlapping codon 12 and an Xcm I restriction site overlapping codon 13 of the wild-type K-ras oncogene.

2. An oligonucleotide primer as claimed in claim 1 wherein said sequence contains a CCA substitution corresponding to the final base of codon 8 and the first two bases of codon 9 of the K-ras gene.

3. An oligonucleotide primer as claimed in claim 2 wherein said sequence comprises the base sequence (SEQ. ID NO. 8):

5' ACTGAATATA AACTTGTGGT CCATGGAGCT 3'.

4. An oligonucleotide primer comprising a sequence for use in in vitro amplification, characterised in that said primer is capable of creating a Bce 83I restriction site overlapping codon 61 of the wild-type K-ras oncogene, and wherein said sequence comprises the base sequence (SEQ. ID NO. 10):

5' TGTCTCTTGG ATATTCTCGA CACAGCAGCT 3'.

5. An oligonucleotide primer as claimed in claim 1 wherein said primer sequence is capable of creating one or more additional restriction sites.

6. An oligonucleotide primer as claimed in claim 5 wherein the additional restriction site is a DraI restriction site upstream of the restriction site overlapping codon 12 and/or codon 13 of the wild-type K-ras oncogene.

7. An oligonucleotide primer as claimed in claim 6 wherein said sequence comprises the base sequence (SEQ. ID NO. 9):

5' ACTGAATTTA AACTTGTGGT CCATGGAGCT 3'.

8. An oligonucleotide primer as claimed in claim 1 wherein the sequence is 22 to 30 nucleotides long.

9. Use of an oligonucleotide primer as claimed in claim 1 and/or claim 4 in an in vitro amplification-based method for detection of activating mutations in codons 12 and/or 13 and/or 61 of the K-ras oncogene.

10. A method of detecting activating mutations in codons 12 and/or 13 and/or 61 of the K-ras oncogene, said method comprising subjecting a sample containing the target K-ras DNA to be detected to one or more cycles of in vitro amplification using as an amplification primer, an oligonucleotide primer as claimed in claim 1 and/or claim 4, followed by restriction endonuclease digestion of wild-type K-ras sequences, using BstX I and/or Xcm I and/or Bce 83I and detecting the said amplified mutant K-ras sequences obtained.

11. A method as claimed in claim 10 wherein restriction endonuclease digestion is followed by one or more further cycles of in vitro amplification whereby mutant K-ras sequences containing said activating mutations are enriched.

12. A method as claimed in claim 10 wherein an additional primer is used for amplification.

13. A method as claimed in claim 12 wherein the sequence of the additional primer is selected from:

5' TTATCTGTAT CAAAGAATGG TCCTGCACCA 3' (SEQ. ID NO. 12) and

5' TATTAAAACA AGATTTAC 3' (SEQ. ID NO. 13).

14. A method as claimed in claim 12 wherein said additional primer is capable of creating at least one restriction site.

15. A method as claimed in claim 14 wherein said additional primer is capable of creating a BstX I and Xcm I restriction sites.

16. A method as claimed in claim 15 wherein said additional primer has the sequence

5' GAATGGTCCT CCACCAGTA TATGGATATT A 5' (SEQ. ID NO. 14).

17. A method as claimed in claim 10 wherein PCR is used for amplification.

18. A kit for the detection of activating mutations in codons 12 and/or 13 and/or 61 of the K-ras oncogenes, comprising at least one oligonucleotide primer as claimed in claim 1 and/or claim 4.

19. A kit as claimed in claim 18 wherein additional components for amplification are provided.

20. A kit as claimed in claim 19 wherein said amplification is performed using a) PCR and the kit additionally comprises a polymerase and at least one other oligonucleotide primer; the oligonucleotides both being DNA based and hybridising to opposite strands of the target DNA; or b) DIANA and the kit additionally comprises a polymerase and PCR oligonucleotide primer sequences as claimed in claim 1 provided with means for immobilisation and means for labelling; or c) 3SR and the kit additionally comprises a reverse transcriptase and a further DNA oligonucleotides primer, both oligonucleotides being provided with a polymerase binding site; or d) Q-beta replicase and the kit additionally comprises an RNA directed RNA polymerase and an RNA probe with a 5'-MDV-1 structure, the capture oligonucleotide being immobilised or permitting immobilisation.

* * * * *